(12) United States Patent
Saksela et al.

(10) Patent No.: US 6,794,144 B1
(45) Date of Patent: Sep. 21, 2004

(54) METHODS AND MATERIALS FOR GENERATING SH3 DOMAINS WITH TAILORED BINDING PROPERTIES

(75) Inventors: Kalle Saksela, Helsinki (FI); Marita Hiipakka, Tampere (FI)

(73) Assignee: Licentia Ltd., Helsinki (FI)

( * ) Notice: Subject to any disclaimer, the term of this patent is extended or adjusted under 35 U.S.C. 154(b) by 0 days.

(21) Appl. No.: 09/579,894

(22) Filed: May 26, 2000

Related U.S. Application Data

(60) Provisional application No. 60/136,085, filed on May 26, 1999.

(51) Int. Cl.[7] .................. G01N 33/53; G01N 33/566
(52) U.S. Cl. ........................... 435/7.1; 436/501
(58) Field of Search ................. 435/7.1; 436/501

(56) References Cited

FOREIGN PATENT DOCUMENTS

| WO | WO9524419 | 9/1995 |
|----|-----------|--------|
| WO | WO9603649 | 2/1996 |

OTHER PUBLICATIONS

Lee et al, The EMBO journal, vol. 14, No. 20, pp. 5006–5012, 1995.*
Hiipakka et al, J. Mol. Biol. 293, 1097–1106, 1999.*
Collette et al, The Jrnl. of Biol. Chem. 275(6), 4171–76, 2000.*
Briggs et al, The Jrnl. of Biol. Chem. 272(29), Jul. 18, 1997.*
Sparks et al., J. Biol. Chem. vol. 269 No. 39 (9/94) pp. 23853–23856.*

* cited by examiner

*Primary Examiner*—Bennett Celsa
(74) *Attorney, Agent, or Firm*—Birch, Stewart, Kolasch & Birch, LLP.

(57) ABSTRACT

The present invention relates to controlled modification of Src homology region 3 (SH3) domains by using random manipulation of the non-conserved region of SH3 RT-loop. Consequently, the invention concerns methods and materials for generating SH3 do-mains with engineered binding properties, and their use as tools in research, diagnostics, therapy and drug discovery.

6 Claims, 4 Drawing Sheets

SEQUENCE LISTING

<160> NUMBER OF SEQ ID NOS: 32

<210> SEQ ID NO 1
<211> LENGTH: 5
<212> TYPE: PRT
<213> ORGANISM: Homo sapiens
<220> FEATURE:
<223> OTHER INFORMATION: consensus motif of SH3 domains

<400> SEQUENCE: 1

Ala Leu Tyr Asp Tyr
 1               5

<210> SEQ ID NO 2
<211> LENGTH: 6
<212> TYPE: PRT
<213> ORGANISM: Homo sapiens
<220> FEATURE:
<223> OTHER INFORMATION: amino acids 14-19 of the human Nck protein

<400> SEQUENCE: 2

Val Ala Gln Gln Glu Gln
 1               5

<210> SEQ ID NO 3
<211> LENGTH: 6
<212> TYPE: PRT
<213> ORGANISM: Mus sp.
<220> FEATURE:
<223> OTHER INFORMATION: amino acids 794-799 of the C-terminal SH3
      domain of mouse Vav1 protein

<400> SEQUENCE: 3

Cys Ala Arg Asp Arg Ser
 1               5

<210> SEQ ID NO 4
<211> LENGTH: 78
<212> TYPE: DNA
<213> ORGANISM: Artificial Sequence
<220> FEATURE:
<223> OTHER INFORMATION: Description of Artificial Sequence:PCR primer
<221> NAME/KEY: unsure
<222> LOCATION: ()..()
<223> OTHER INFORMATION: any n = c, g, a, t

<400> SEQUENCE: 4
attctgcagg aattcgtggt tgccctgtat gattatnnnn nknnsnnknn knnsgacctc      60
agcttccaga aggggac                                                    78

<210> SEQ ID NO 5
<211> LENGTH: 6

```
<212> TYPE: PRT
<213> ORGANISM: Homo sapiens
<220> FEATURE:
<223> OTHER INFORMATION: amino acid residues 69-74 of human p59 Hck
      protein

<400> SEQUENCE: 5

Glu Ala Ile His His Glu
  1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence:Modified
      RT-loop sequence

<400> SEQUENCE: 6

Val Ser Trp Ser Pro Asp
  1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence:Modified
      RT-loop sequence

<400> SEQUENCE: 7

Phe Ser Trp Ser Asp Thr
  1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence:Modified
      RT-loop sequence

<400> SEQUENCE: 8

Asp Ser Trp Ser Thr Ser
  1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence:Modified
      RT-loop sequence

<400> SEQUENCE: 9

Tyr Ser Trp Ser Asp Met
  1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence:Modified
      RT-loop sequence

<400> SEQUENCE: 10

Trp Ser Pro Phe Pro Ser
```

```
1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence:Modified
      RT-loop sequence

<400> SEQUENCE: 11

Asp Ser Pro Phe Ser Phe
 1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence:Modified
      RT-loop sequence

<400> SEQUENCE: 12

Phe Ser Pro Phe Ser Phe
 1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence:Modified
      RT-loop sequence

<400> SEQUENCE: 13

Phe Ser Pro Phe Asp Trp
 1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence:Modified
      RT-loop sequence

<400> SEQUENCE: 14

Ser Ser Pro Phe Asp Trp
 1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence:Modified
      RT-loop sequence

<400> SEQUENCE: 15

Tyr Ser Pro Phe Ser Trp
 1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence:Modified
```

```
                          RT-loop sequence

<400> SEQUENCE: 16

Thr Ser Pro Phe Pro Trp
 1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence:Modified
      RT-loop sequence

<400> SEQUENCE: 17

Tyr Ser Phe Phe Pro Trp
 1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence:Modified
      RT-loop sequence

<400> SEQUENCE: 18

Tyr Ser Asp Phe Pro Trp
 1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence:Modified
      RT-loop sequence

<400> SEQUENCE: 19

Asp Ser Trp Phe Pro Trp
 1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence:Modified
      RT-loop sequence

<400> SEQUENCE: 20

Ser Ser Phe Tyr Ser Ser
 1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence:Modified
      RT-loop sequence

<400> SEQUENCE: 21

Gln Gly Phe Leu Asp Gln
 1               5

<210> SEQ ID NO 22
```

```
<211> LENGTH: 6
<212> TYPE: PRT
<213> ORGANISM: Artificial Sequence
<220> FEATURE:
<223> OTHER INFORMATION: Description of Artificial Sequence:Modified
      RT-loop sequence

<400> SEQUENCE: 22

Asn Ala Phe Leu Pro Ser
 1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence:Modified
      RT-loop sequence

<400> SEQUENCE: 23

Glu Ala Trp Ser Pro Leu
 1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence:Modified
      RT-loop sequence

<400> SEQUENCE: 24

Glu Ser Tyr Ser Glu Trp
 1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence:PXXP motif
      consensus sequence
<223> OTHER INFORMATION: Position 2, 5, 6 = Xaa = any amino acid
<223> OTHER INFORMATION: Position 3 = Xaa = a hydrophobic amino acid

<400> SEQUENCE: 25

Arg Xaa Xaa Pro Xaa Xaa Pro
 1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence:PXXP motif
      consensus sequence
<223> OTHER INFORMATION: Position 2, 5 = Xaa = any amino acid
<223> OTHER INFORMATION: Position 3 = Xaa = a hydrophobic amino acid

<400> SEQUENCE: 26

Pro Xaa Xaa Pro Xaa Arg
 1               5

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence:fragment of
```

56aa Hck polypeptide fragment

<400> SEQUENCE: 27

Val Asp Ser Leu
 1

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence:artificial
      SH3 domain - peptide motif
<223> OTHER INFORMATION: Position 1, 5, 6 = Xaa = any amino acid

<400> SEQUENCE: 28

Xaa Ser Trp Ser Xaa Xaa
 1               5

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence:artificial
      SH3 domain - peptide motif
<223> OTHER INFORMATION: Position 1, 5, 6 = Xaa = Val, Phe, Asp, Met,
      Pro, Ser, Thr, Trp, or Tyr

<400> SEQUENCE: 29

Xaa Ser Trp Ser Xaa Xaa
 1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence:artificial
      SH3 domain - peptide motif
<223> OTHER INFORMATION: Position 1, 5, 6 = Xaa = any amino acid

<400> SEQUENCE: 30

Xaa Ser Pro Phe Xaa Xaa
 1               5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence:artificial
      SH3 domain - peptide motif
<223> OTHER INFORMATION: Position 1, 5, 6 = Xaa = Val, Phe, Asp, Met,
      Pro, Ser, Thr, Trp, or Tyr

<400> SEQUENCE: 31

Xaa Ser Pro Phe Xaa Xaa
 1               5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence:artificial
      SH3 domain - peptide motif
<221> NAME/KEY: UNSURE
<222> LOCATION: (1)..(3)

```
-continued

<223> OTHER INFORMATION: any Xaa = unknown

<400> SEQUENCE: 32

Xaa Ser Xaa Phe Pro Trp
 1               5
```

METHODS AND MATERIALS FOR GENERATING SH3 DOMAINS WITH TAILORED BINDING PROPERTIES

This application claims the benefit of Provisional application Ser. No. 60/136,085, filed May 26, 1999.

FIELD OF THE INVENTION

A number of biological processes that are important for normal and pathological states are governed by interactions of cellular proteins mediated by Src homology region 3 (SH3) domains. This disclosure concerns methods and materials for generating SH3 domains with engineered binding properties, and their use as tools in research, therapy, diagnostics and drug discovery.

BACKGROUND OF THE INVENTION

Virtually all aspects of cellular behavior, such as adaptation of a cell in response to extracellular stimuli by changing of its pattern of gene expression, are regulated and executed by dynamic and ordered proximity of cellular proteins. During the evolution several different types of protein domains specialized in mediating such regulated and specific protein-protein interaction events have emerged. Protein domains of one type typically form large families of homologous but sufficiently divergent members, such that each of them have unique, although often overlapping specificities for ligand binding.

The SH3 domain was first identified as a region of homology among the Src family tyrosine kinases encoded by oncogenic retroviruses and their cellular proto-oncogene counterparts. Thereafter SH3 domains have been noticed in a large number (>50) of proteins that serve important functions in regulating cell growth, differentiation, and other processes. Because of these functions SH3 domains are intimately involved in pathogenes is of various diseases, in particular cancer. In addition, various microbial pathogens, such as HIV, exploit SH3-mediated processes as a part of their life-cycle. Ability to influence protein complex formation mediated by SH3 domains would therefore have significant therapeutic potential.

SH3 domains are globular protein modules typically consisting of 50–70 amino acids found in many different proteins, particularly proteins involved in cellular signal transduction (Cohen et al. 1995. Cell, 80, 237–248; Dalgarno et al. 1997. Biopolymers, 43, 383–400). SH3 domains mediate inter- and intramolecular interactions by binding to ligands that contain a region with a secondary structure known as the polyproline type II (PPII) helix. These ligands can bind to SH3 domains in two oposite orientations and typically show the "PxxP motif" consensus sequences RX∅PXXP (SEQ ID NO: 25) and PX∅PXP (∅ is a hydrophobic amino acid, X is any amino acid) (Feng et al. 1994. Science, 266, 1241–7; Lim et al. 1994. Nature, 372, 375–9). The positioning of the conserved basic residue (usually an arginine, R) in the PxxP motif determines in which orientation the ligand binds its cognate SH3 domain. In addition, there are arypical SH3-ligands with PPII helices that do not conform to such consensus rules. A notable example is the PPII region in Src, which is involved in catalytic autoinhibition by binding to the SH3 domain of Src itself, but contains only one of the two prolines that ordinarily define a PxxP-motif (Xu et al. 1997. Nature, 385, 595–602).

Sequence variation in the PPII helix region involving the consensus as well as the adjacent, non-consensus positions, has been shown to influence the specificity in SH3/ligand complex formation. Examples of preference for targets with atypical PxxP consensus motifs have been provided by studies addressing Abl SH3 ligand selection (Feng et al. 1994. Science, 266, 1241–7; Weng et al. 1995. Mol Cell Biol, 15, 5627–34; Yu at al. 1994. Cell, 76, 933–945), and the CrkN-SH3/C3G peptide complex (Knudsen et al. 1995. EMBO J, 14, 2191–8; Wu at al. 1995. Structure, 3, 216–226). The effect of sequence variation involving the non-consensus residues in the PPII region of SH3-ligands has been best demonstrated by experiments in which distinctive target sequences have been selected for different SH3 domains from libraries of chemically synthesized or phage-displayed random peptides (Sparks et al. 1994. J Biol Chem, 269, 23853–6; Viguera et al. 1994. Biochemistry, 33, 10925–33; Yu at al. 1994. Cell. 76, 933–45). However, despite the above-discussed evidence for specificity, the maximal SH3-binding affinities of short PPII ligand peptides are low, and the relative differences in their binding to different SH3 domains are modest.

By contrast, there is increasing evidence that molecular contacts outside the PPII helix interface can provide significant specificity and strength to SH3-binding. Use of phage-display libraries of longer peptides containing a PxxP motif embedded within random sequence has demonstrated that the flanking residues can increase the selectivity of such ligands, which may show up to 20-to-30 fold differences in their affinities towards different SH3 domains (Rickles et al. 1994. EMBO J, 13, 5598–604; Rickles et al. 1995. Proc Natl Acad Sci U S A, 92, 10909–13, Sparks et al. 1996. Proc Natl Acad Sci U S A, 93, 1540–4). Structural analysis of the interactions of Src-SH3 with two such dodecapeptides revealed that the relatively high specificity and affinity ($K_D$ values 0.54 $\mu$M and 1.2 $\mu$M) of these interactions involved contacts between the flanking residues in the peptides and two loop-like structures in the Src-SH13 domain, which represent regions of high sequence diversity among different SH3 domains and are known as the n-src- and RT-loops (Feng et al. 1995. Proc Natl Acad Sci U S A. 92, 12408–15). Similarly, the sepecific binding of a rationally designed proline-rich ligand to Abl SH3 ($K_D$ 0.4 $\mu$M for Abl vs. 273 $\mu$M for Fyn-SH3) could be explained by corresponding molecular contacts with Abl SH3 (Pisabarro and Serrano, 1906. Biochemistry, 35, 10634–40; Pisabarro et al. 1998. J Mol Biol, 281, 513–521).

Another interaction that has been informative in elucidating the basis of SH3 binding specificity, which also emphasizes the role of the RT-loop, is the complex between HIV-1 Nef and the SH3 domain of the tyrosine kinase Hck. Nef is a 27–34 kD myristoylated protein of primate lentiviruses (HIV-1, -2, and SIVs), and important for development of high viremia and immunodeficiency in the infected host (Harris, 1996. J Gen Virol, 77, 2379–92; Saksela, 1997. Front Biosci, 2, 606–618). Interestingly, Nef has remarkably selective SH3-binding characteristics. It can bind tightly to the Hck-SH3, showing affinity values of approximately $K_D$ 0.2 $\mu$M as measured by surface plasmon resonance (Lee at al. 1995. EMBO J, 14, 5006–15). In contrast to the strong binding to Hck, Nef has almost a 100-fold lower affinity towards the highly homologous SH3 domain of Fyn. Biochemical and structural studies have revealed that the basis of this selectivity lies in the efficient strategy of Nef for recognition of the non-conserved SH3 residues distinctive to Hck, in particular the side chain of an isoleucine located in the RT-loop of Hck-SH3 (Lee et al. 1996. Cell, 85, 931–942). The region that accommodates the Hck-SH3 RT-loop is composed of multiple non-contiguous parts of the Nef polypeptide, and is located distally from the PPII region in the three-dimensional structure of Nef.

Previous attempts to generate molecules that could compete with naturally occurring SH3-interactions have focused on design or selection from random libraries of peptides and peptide-like molecules that could compete with PPII ligands for their binding to their cognate SH3 domains. Success in such approaches has been reported by a number of groups (see references above). Patent applications for different modifications of this approach have been filed (such as WO 95/24419 and WO 96/03649). However, the relative similarity of the SH3/PPII interface of different SH3/ligand pairs presents a problem far developing highly specific inhibitory molecules. To overcome this problem we have chosen a different approach, which is based on the apparent role of the SH3 domain RT-loop in ligand selection that has been indicated by a number of studies, in particular our previous work on the complex between the HIV Nef protein and the SH3 domain of the cellular Hck tyrosine kinase.

The above observations suggest a general mode where regions in SH3 ligands outside the PPII helix region provide specificity and affinity for binding by contacting regions that are divergent among SH3 domains, in particular residues in the RT-loop. Prompted by this concept, in the present invention we have constructed a large library (>130 millions) of Hck-derived artificial SH3 domains, in which six non-conserved, Hck-specific residues in the RT-loop have been replaced by a random hexapeptide (termed RRT-SH3 for randomized RT-loop, and expressed these on the surface M13 bacteriophages in order to identify novel SH3 domains with engineered binding characteristics. We show that phage-display is well suited for presentation and selection of modified SH3 domains, and provide strong experimental support for a role of the SH3 RT-loop as a versatile specificity and affinity determinant.

Consequently, as explained hereinbelow, we have found that by randomly manipulating the amino acid sequence comprising the variable region of the RT-loop (in this case six amino acids of the Hck SH3 domain) it is possible to create artificial SH3 domains that bind with unnaturally high affinities and with predetermined binding specificities to different ligand proteins.

SUMMARY OF THE INVENTION

The well-characterized interaction between HIV-1 Nef and the SH3 domain of Hck is one of the tightest known SH3-mediated interactions. We have previously shown that a similar capacity for binding to Nef can be transferred to Fyn-SH3 by engineering Hck-like amino acid substitutions into its RT-loop. The present invention is in the finding that, instead of mimicking the structure of a naturally occurring, known cognate SH3 domain, one can generate SH3 domains with desired ligand binding properties by using random manipulation of the RT-loop sequence combined with a powerful affinity or functional selection. Notably the method described in this invention can be used to identify SH3 domains with unnaturally high affinities specific for proteins known to bind to any naturally occurring SH3 domains, as well as to target proteins that are believed to be SH3 ligands but lack an identified SH3 domain-containing cellular partner.

Consequently, the present invention provides a method for generating SH3 domains with tailored binding properties, artificial SH3 domains (termed RRT-SH3 domains) obtained by such a method for use as efficient took in research, diagnostics, therapy and drug discovery.

DETAILED DESCRIPTION OF THE INVENTION

Figure 1:
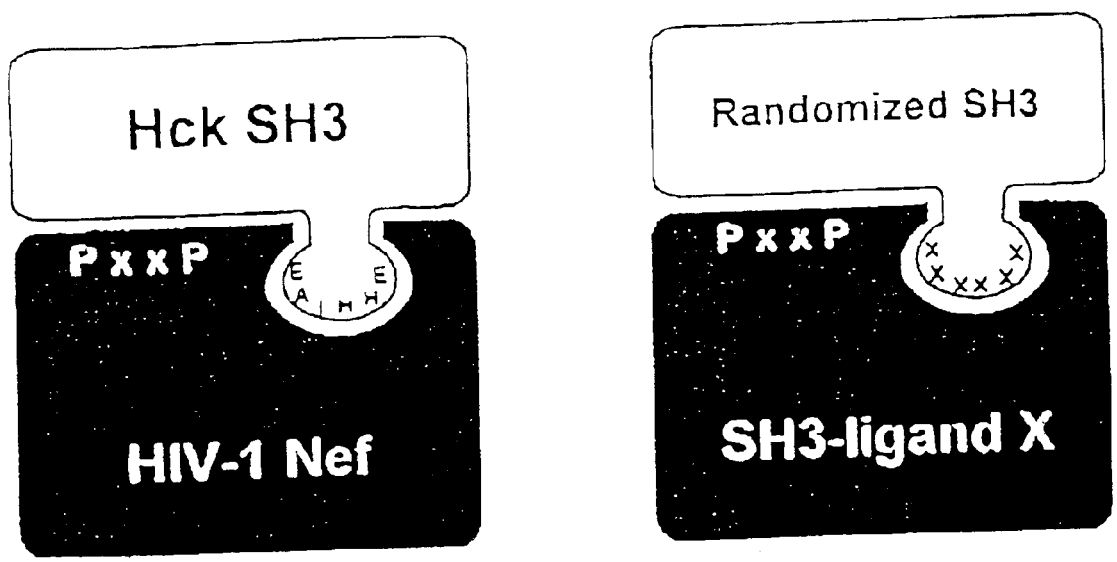
FIG. 1. A simplified cartoon depicting the strategy of current invention for creating SH3 domains with altered binding properties. Interactions of SH3 domains, such as Hck-SH3, with their cognate ligand proteins involve a set of molecular contacts between the SH3 domain and a proline repeat (PxxP) motif region in the ligand protein. Although necessary for binding, these PxxP-directed interactions are weak and relatively similar in most SH3/ligand complexes, and therefore provide little selectivity and strength for these interactions.

In the prototypic version of the invention presented here we have used polymerase chain reaction (PCR) assisted mutagenesis to produce a large collection of SH3 domains (termed RRT-SH3) that shared their overall structure with Hck-SH3, but contained a random combination of amino acids in place of the six RT-loop residues that constitute a variable region among the otherwise homologous SH3 domains. We generated=130 million individual recombinant phagemid-expressed RRT-SH3 domains, which exceeds the theoretical number of all possible combinations of six residue peptides made of the 20 different amino acids ($20^6$=64 million). We discovered that a method known as phage-display is well-suited for expression of functional SH3 domains on the surface of bacteriophage particles, and used this method as a selection tool for identification of the rare RRT-SH3 domains with desired binding properties from among the millions of non-binding molecules. Although at the moment phage-display appears to be the preferred method for such functional selection of the RRT-SH3 domains, the current invention is not restricted to this approach, and a number of other methods could also be used for this task.

As a proof of principle for the usefulness of this approach we showed that it is possible to identify individual RRT-SH3's which bound to HIV-1 Nef with up to 40-fold higher affinities than the already avidly binding ($K_D$ 250 nM) Hck-SH3 domain that served as the backbone of the artificial RRT-SH3 molecules. Such superior affinity provided these molecules an ability to efficiently compete with the Hck/Nef interaction even when present in low concentrations, thus pointing out to obvious therapeutic applications. Notably, we showed that it is possible to identify RRT-SH3 molecules from this Hck-derived library that bind with very high affinities to SH3 ligand protein that do not have significant affinity for the natural, unmodified Hck-SH3. As an example of such a protein we used a mutant version of the Nef protein (NefR90) whose ability to bind Hck-SH3 has been disturbed by a mutation that specifically prevents the accommodation of the native Hck-SH3 RT-loop. These proof-of-principle studies are described below in Example 1 together with methodological details of this prototypic application of the invention.

The present invention provides a generally useful method for targeting of SH3 ligand proteins with artificial SH3 domains. Although our results indicate that very different binding specificities can be generated by manipulation of the SH3 RT-loop of a single (Hck) SH3 domain backbone structure, other SH3 domains can be similarly modified by the described methodology, if necessary in order to create high affinity molecules for all SH3 ligand proteins. Also, the engineering of the binding-properties by manipulation of the RT-loop region could be combined with other random or specific modifications of the SH3 domain to further optimize its binding or other physico-chemical properties, such as protease resistance or solubility.

Instead of targeting individual, known SH3 target proteins in vitro, RRT-SH3 libraries may also be used to target yet unknown SH3 target proteins that serve important roles in cellular events of interest, such as proliferation and programmed cell death. In this approach, an RRT-SH3 library is introduced into cultured cells using vectors such as recombinant retroviruses, and a cell with a phenotype of interest is selected from among a large population of cells expressing different RRT-SH3 domains, as is routinely done in a strategy well known as "functional cloning", where libraries of cell-derived cDNAs instead of RRT-SH3 domain constructs have been introduced into cells. Isolation of the RRT-SH3 domain responsible for the altered cellular phenotype call then be isolated, and used for similar applications as the RRT-SH3 domains discovered by in vitro affinity selection, as well as employed for identification of its specific target protein, which could be a previously unknown SH3-target protein or an already recognized protein that has previously not known to be involved in functions related to the altered phenotype of interest that was selected for.

Several valuable applications for tailor-made SH3 domains described by the present invention can be envisioned. They could be introduced into and expressed in cells in order to activate, inhibit or otherwise regulate or modify the functions of SH3-ligand proteins and their complexes with other proteins. If the RRT-SH3 domains would be equipped with a protein with an appropriate targeting signal, the subcellular localization of their target protein could also be influenced this way. Further, a diagnostic method could be designed for the detection of infectious organisms, detecting the binding of the RRT-SH3 domains to their targets, such as viral proteins, either in cells or cell-free systems.

While the most apparent uses of such approaches are in basic research on SH3-mediated cellular processes, similar applications in gene therapy are also obvious. The relatively small size of an SH3 domain also makes it possible that the engineered RRT-SH3 proteins could be delivered into target cells by fusing them to membrane-penetrating peptides or other such methods. Besides being used as therapeutic agents themselves, structural analysis of the RRT-SH3/ligand complexes could also help in design of non-peptide compounds targeted against the SH3-binding interfaces of various disease-associated cellular proteins. It would thus be possible to design drug, candidates stucturally mimicking tile RRT-SH3 domains and sharing similar binding properties.

Finally, the ability of RRT-SH3 to interact tightly to the SH3-binding surface of the ligand proteins, and thereby compete with any compounds that bind to the same region, could also be helpful in identifying molecules derived by non-rational drug discovery screens that are targeted against these functionally important regions. It would thus be possible to guide drug development by using a RRT-SH3 to recognize the molecular region in its traget protein that should be targeted by a drug in order to prevent similar interactions of this protein with naturally occurring SH3 domains.

The six SH3 amino acid residues to be replaced according to the invention by an artificial amino acid sequence to generate RRT-SH3 domains correspond to the residues 69 to 74 (EAIHHE) SEQ ID NO: 5 in the human p59 Hck protein sequence (GenBank PID: 2144421), and form the exposed part of a SH3 structure known as the RT-loop. Although SH3 domains are divergent in their amino acid sequence in this region, analogous residues are present in the RT-loops of all other SH3 domains as well. In other SH3 domains these analogous, amino acids can be specified as the residues occupying the six consecutive positions in the polypeptide chain that immediately follow a conserved stretch of amino acids referred to as the ALYDY SEQ ID NO: 1 consensus motif, because this or related sequence can be identified by amino acid alignment in virtually all SH3 domains. For example, in the most amino terminal of the three SH3 domains of the human Nck protein (GenBank PID:88235) these residues are VAQQEQ SEQ ID NO: 2 and occupy the amino acid positions 14 to 19, whereas in the carboxy terminal SH3 domain of the mouse Vav1 protein (GenBank PID: 6755955) these residues are CARDRS SEQ ID NO: 3 and occupy the amino acid positions 794 to 799.

The RRT-SH3 domains obtained can be further modified in their structure, e.g. by shortening the amino acid sequence thereof, without affecting their function, to obtain derivatives of RRT-SH3 domains. Such derivatives may have advantageous properties for expression in cells.

As an example of generating SH3 domains with tailored binding properties we describe below in detail generation of SH3 domains derived from Hck-SH3, being targeted to the HIV-1 Nef protein.

EXAMPLE 1

SH3 Domains Targeted with High Affinity to Wild-type and Hck-SH3 Binding-deficient forms of HIV-1 Nef Methods Generation of Hck-SH3-containing Phagemid Vectors To produce a phagemid for expression of native Hck-SH3 a DNA ferment encoding a 56 aa Hck polypeptide fragment (NH$_2$—VV . . . VDSL-SEQ ID NO: 27COOH) was amplified by PCR using Pfu polymerase (Stratagene) and primers containing Pst I and Not I sites, and inserted into the corresponding sites in pCANTAB-5EP, a modified version of pCANTAB-5E (Pharmacia) with a new Pst I cloning site. To create the library of RRT-SH3 domains, a longer sense PCR primer 5'-AAT CTG CAG GAA TTC GTG GTT GCC CTG TAT GAT TAT NNN NNK NNS GAC CTC AGC TTC CAG AAG GGG GAC-3' SEQ ID NO: 4 extending over the RT-loop encoding region of Hck was used (N=C/G/T/A, S=G/C and K=G/T), and the resulting fragment was cloned into pCANTAB-5EP as described above. A total of 137×10$^6$ individual recombinant colonies were obtained by electroporation into *E. coli* TG1 cells, which were pooled and infected with the M13KO7 helper phage as explained below.

Production of Infectious Recombinant Phages

Overnight cultures of TG1 cells carrying the phagemid(s) of interest were grown at 30° C. in 2×YT containing 100 μg/ml ampicillin and 2% glucose (2×YT/AG). Cultures were diluted 1/10 in 2×YT/AG, and incubated with 5×10$^8$ pfu/ml of M13KO7 helper phage (Pharmacia) for 2 hours at 37° C. The bacteria were pelleted, and the medium changed to 2×YT containing 100 μg/ml ampicillin and 50 μg/ml kanamycin (2×YT/AK). After overnight growth of the double resistant bacteria in this medium at 37° C., the supernatant containing the recombinant phages was collected, pasted through a 0.45 μm filter, and stored in aliquots at 4° C. until needed.

Phage Selection

Six-well plates were coated with 10 μg/ml GST-Nef (HIV-1 NL4-3 Nef containing a T71R change to mimic Nef from typical primary HIV-1 isolates; Saksela at al., 1995. EMBO J, 14, 484–91), GST-NefR90 (see text; Manninen et al. 1998. Virology, 250, 273–82), GST-Nef-PA1 (P72A+P75A mutant of Nef; Saksela et al. 1995. EMBO J, 14, 484–91) or plain GST in 50 mM sodium carbonate pH 9.6 at 4° C. overnight. Nonspecific binding sites were blocked with 5% milk in PBS/0.05% Tween 20, and the wells washed briefly with PBS before 10$^7$–10$^{11}$ pfu of recombinant phages per well were added (higher titers used in the early rounds of selection), followed by incubation for 2 hours at RT. In some experiments involving NefR90-coated wells, the phage solution was supplemented with 10 μg/ml of soluble wild-type Nef. After incubation with the phages the wells were washed six times (5 min) with PBS+0.05% Tween 20 and three times with PBS.

In most experiments the bound phages were eluted with a small volume of PBS containing an excess of (150 μg/ml) of the same Nef protein immobilized in the well. Alternatively, the TG1 cells to be infected were added directly to the washed wells. In both cases, the bacteria were first grown in 2×YT to log phase from an overnight culture, infected with the affinity-selected phages for 2 hours at 37 ° C., after which a sample of 1% was removed for determination of the infectious titer of the selected phages by plating on ampicillin plates. These plates also served as indicators for the enrichment of specific clones when compared to plates infected with phages from GST-coated wells processed in parallel. The remaining 99% of the infected bacteria were supplemented with 100 μg/ml ampicillin and 2% glucose, and subjected to a subsequent infection with 5×10$^8$ pfu/ml of M13KO7 helper phages for 2 hours at 37° C., after which they were pelleted and resuspended into an equal volume of 2×YT/AK. After an overnight incubation the amplified recombinant phage supernatants were collected as described above, and used for the subsequent round of selection/infection. Usually after 8 cycles of selection >12 colonies were picked for miniprep preparation of phagemid DNA, and their RRT-SH3 insert sequenced using ABI Prism 310 (Perkin Elmer Applied Biosystems).

Expression of Recombinant Proteins

Generation of the pGEX vector for bacterial expression of the GST fusion proteins for Nef and Hck-SH3 has been described previously (Saksela et al. 1995. EMBO J, 14, 484–491; Manninen at al. 1998. Virology, 250, 273–282). GST-RRT-SH3 vectors were constructed by PCR amplification of the SH3 fragments from the corresponding phagemids, and insertion between the Eco RI and Sal I sites in pGEX-4T-1 (Pharmacia), and verified by sequencing. Expression and purification of the GST fusion proteins in *E. coli* BL21 were carried out by standard methods as recommended by the supplier of the pGEX vectors and glutathione resin (Pharmacia). After elution of the fusion proteins from the resin they were concentrated and their buffer changed to PBS by ultrafiltration in Centrex UF2 columns (Schleicher & Schuell), followed by concentrations measurement using the BioRad (Lowry) method using BSA as a standard. The concentration and integrity of the proteins were further confirmed in Coomassie blue stained SDS PAGE gels. Biotinylation was done using the EZ-Link Sulfo-NHS-LC-Biotin reagent, as suggested by the manufacturer (Pierce), after which these proteins were subjected to 3 rounds of ultrafiltration to remove any free biotin, followed by concentration measurement as described above.

Competitive Nef/SH3 Binding Assay

Nunc Maxisorb F8 strips were coated with the different GST-Nef proteins (200 ng in 100 μl per well) overnight at 4° C., followed by a 30 min incubation at RT with 1.5% BSA in washing buffer (WB; PBS+0.05% Tween-20) to saturate non-specific protein binding, and washed twice with WB. The unlabeled SH3 proteins used as competitors were diluted into WB that contained 1.5% BSA and a large molar excess of plain GST (4 μM) to minimize any GST-directed dimerization of the fusion proteins. 50 μl of this solution was mixed with an equal volume of the probe (biotinylated SH3 in WB) and added to die wells resulting in a final probe concentration of 66 μM (Hck-SH3/Nef and RRT.A1/NefR90 assays) or 7 nM (RRT.A1/Nef assay). After a 1 hour incubation at RT the wells were washed three times with WB, and added 100 μl of 1:2000 dilution (in WB) of streptavidin-biotin horseradish peroxidase complex (Amersham Life Sciences) per well. The plates were incubated 45 minutes at RT and washed again three times, after which their peroxidase activity was measured using 1,2-phenylenediamine-dihydrochloride (OPD; 0.6 μg/ml; Fluka AB) as a substrate. The enzymatic reactions were stopped after 10 minutes by adding 50 μl of 2 M sulfuric acid, followed by optical density measurement at 492 nm using a Victor 1420 Multilabel Counter (Wallac).

Results

The avid binding of HIV-1 Nef to the Src homology-3 (SH3) domain of Hck ($K_D$ 250 nM) has been shown to involve an interaction between the RT-loop of Hck-SH3 and residues in Nef outside of its prototypic polyproline type 11 (PPII) helix-containing SH3-ligand region. Such distinctive interactions are thought to provide specificity and affinity for other SH3/ligand protein complexes as well. In this invention we constructed and successfully displayed on the surface of M13 bacteriophage particles a complex library of SH3 domains, which are derived from Hck but carry a random hexapeptide substitution in their RT-loops (termed RRT-SH3). By this strategy we identified individual RRT-SH3 domains that can bind to Nef with affinities higher than $K_D$ 10 nM. Some of these high-affinity RRT-SH3 domains resembled Hck-SH3 in that they bound much less well to a Nef variant containing an engineered F90R mutation that interferes with docking of the native Hck RT-loop. In addition, we could also select RRT-SH3 domains with an opposite specificity, which were dependent on the Arg$^{90}$ residue for strong binding, and had a 100-fold lower affinity for unmodified Nef. These results emphasize the importance of the RT-loop in SH3 ligand selection, and suggest a general strategy for creating SH3 domains with desired binding properties.

Generation of a Phage-display RRT-SH3 Library

To examine if it would be possible to present functional SH3-domains on the surface of bacteriophages we constructed phagemid containing Hck-SH3, and by using a M13KO7 helper virus produced recombinant phages expressing it fused to the pIII coat protein. When these phages were incubated in six-well plates coated with purified GST-Nef, GST-Nef-PA1 (an SH3 binding deficient P72A;P75A mutant of Nef), or plain GST protein, the titers of infectious phage-particles resisting washes were found to be 2 to 3 orders of magnitude higher in the GST-Nef coated wells as compared to wells coated with plain GST or with the GST-Nef-PA1 fusion protein (data not shown). Thus, these results indicated that functional SH3 domains can be displayed on the surface of M13 phage particles, and that such phases can be positively selected using a cognate SH3 ligand as an affinity reagent.

To create SH3 domains wish novel ligand binding properties, we used PCR-assisted mutagenesis to produce a large collection of SH3 domains (termed RRT-SH3) that shared their overall structure with Hck-SH3 but contained a random combination of amino acids in place of the six RT-loop residues (EAIHHE) that constitute a variable region among the otherwise homologous SH3 domains. We generated=130 million individual recombinant phagemid clones expressing different RRT-SH3 domains, which exceeds the theoretical number of all possible combinations of six residue peptides made of 20 different amino acids ($20^6$=64 million). An infectious phage stock displaying this heterogeneous population of RRT-SH3 proteins was generated, as explained above for the Hck-SH3-expressing phagemid, and used for subsequent affinity selection experiments.

Selection of RRT-SH3 Proteins Binding to Nef

To test if the RRT-SH3 library contained novel Nef-binding SH3 proteins, we carried out an extensive selection of phages showing affinity for wild-type HIV-1 Nef. The selection scheme consisted of multiple (11 in all) independent experiments consisting of 7 or 8 rounds of affinity-selection and helper virus-assisted reamplification of the recombinant phages. A representative collection of RRT-SH3 clones derived from different rounds of phage selection were sequenced to follow the loss of heterogeneity in the population and the emergence of putative Nef-binding RRT-SH3 clones. A total of 278 RRT-SH3 clones selected using Nef were sequenced (Table I and data not shown). After six rounds of selection, the phage populations were typically dominated by 1–3 different RRT-SH3 clones. In most cases these dominant clones were identical or similar to the clones derived from other independent experiments, leading us to believe that we had rather exhaustively sampled the library for SH3 domains capable of high-affinity binding to HIV-1 Nef.

The RT-loop sequences of the RRT-SH3 clones found to be dominant after ≧7 rounds of selection are listed in Table I. They fell into four sequence families characterized by three or more identical residues within each class. In addition, these families also shared obvious similarities, most notably a serine residue in the second of the six (2/6) randomized positions present in all of them. One prevalent clone (RRT.C1) contained the consensus motifs of two different RT-loop sequences families (B and C). Besides the frequent appearance of serine, these RT-loops were remarkably rich in aromatic and proline residues. Although the RT-loop of the natural Nef ligand, Hck-SH13, also contains two aromatic residues (hislidines) the selected RT-loop sequence did not bear obvious resemblance to this region in Hck-SH3, or any other naturally occurring SH3 domain in the GenBank database.

TABLE I

RT-loop sequences and binding of the corresponding SH3 domains to Nef and NefR90

| SH3 domain | RT-loop | Hck-SH3 as the probe Ratio of competitor per probe giving 50% inhibition with Nef as the ligand | RRT.A1 as the probe Inhibition at an equimolar probe:competitor ratio Nef as the ligand: | NefR90 as the ligand: |
|---|---|---|---|---|
| Hck-SH3 | E A I H H E | SEQ ID NO. 5 1:1 | <5% | <5% |
| RRT.A1 | V S W S P D | SEQ ID NO. 6 1:35 | 55% | 52% |
| RRT.A2 | F S W S D T | SEQ ID NO. 7 1:19 | 20% | 53% |
| RRT.A3 | D S W S T S | SEQ ID NO. 8 | | |
| RRT.A4 | Y S W S D M | SEQ ID NO. 9 1:10 | 34% | 44% |
| RRT.B1 | W S P F P S | SEQ ID NO. 10 1:26 | 41% | 9% |
| RRT.B2 | D S P F S F | SEQ ID NO. 11 1:22 | 22% | 26% |
| RRT.B3 | F S P F S F | SEQ ID NO. 12 | | |
| RRT.B4 | F S P F D W | SEQ ID NO. 13 1:21 | 41% | 37% |
| RRT.B5 | S S P F D W | SEQ ID NO. 14 | | |
| RRT.B6 | Y S P F S W | SEQ ID NO. 15 1:37 | 51% | 14% |
| RRT.C1 | T S P F P W | SEQ ID NO. 16 1:31 | 39% | <5% |
| RRT.C2 | Y S F F P W | SEQ ID NO. 17 1:16 | 20% | 13% |
| RRT.C3 | Y S D F P W | SEQ ID NO. 18 1:26 | 42% | 20% |
| RRT.C4 | D S W F P W | SEQ ID NO. 19 1:14 | 10% | 19% |
| RRT.D1 | S S F Y S S | SEQ ID NO. 20 1:22 | 45% | 17% |
| RRT.m1 | Q G F L D Q | SEQ ID NO. 21 1:0.8 | <5% | 73% |
| RRT.m2 | N A F L P S | SEQ ID NO. 22 1:2 | <5% | 73% |
| RRT.m3 | E A W S P L | SEQ ID NO. 23 1:17 | 22% | 62% |
| RRT.m4 | E S Y S E W | SEQ ID NO. 24 0:8 | <5% | 46% |

When the RRT-SH3 phage supernatants from the late rounds of selection, which were dominated by the clones shown in Table 1, were subjected to an additional round, of affinity selection using wild-type Nef and the SH3-binding-negative Nef-PA1 mutant in parallel, efficient capture of recombinant phages was seen only in the former case, whereas phage recovery from the Nef-PA1-coated wells did not differ from the control wells without Nef (data not shown). Thus, while the RT-loop sequences of the enriched RRT-SH3 phages provided them with a superior affinity for Nef as compared to the rest of the clones in the library, these interactions were critically dependent on an intact PxxP-motif in Ncf, as expected for bona fide SH3-mediated binding.

RRT-SH3 Domains can Bind to Nef with High Affinity

To study the binding properties of the selected RRT-SH3 domains in more detail, we transferred several members from each of the clone families into a bacterial expression vector to be produced for biochemical studies. To estimate their affinities for Nef we developed a competitive 96-well plate binding assay. In this assay serial dilutions of RRT-SH3 proteins were tested for their ability to compete with a constant amount of gas biotinylated Hck-SH3 for binding to immobilized Nef, followed by calorimetric quantitation of bound Hck-SH3. The binding affinities of the different RRT-SH3 proteins used as competitors could then be easily calculated based on the well-characterized $K_D$ value (250 nM) of the Hck-SH3/Nef interaction. This assay design was chosen because it should be relatively insensitive to most potential sources of error that might easily affect a non-competitive assay, such as effects caused by the GST part of the SH3 fusion proteins or related to the incubation and washing conditions. The validity of this assay was strongly supported by the excellent correlation of the theoretical and experimental values for a homotypic competition of unlabeled Hck-SH3 with biotinylated Hck-SH3, showing close to 50% inhibition at 1:1 ratio, and expected values over a wide range of concentration ratios (FIG. 2A).

Figure 2A:
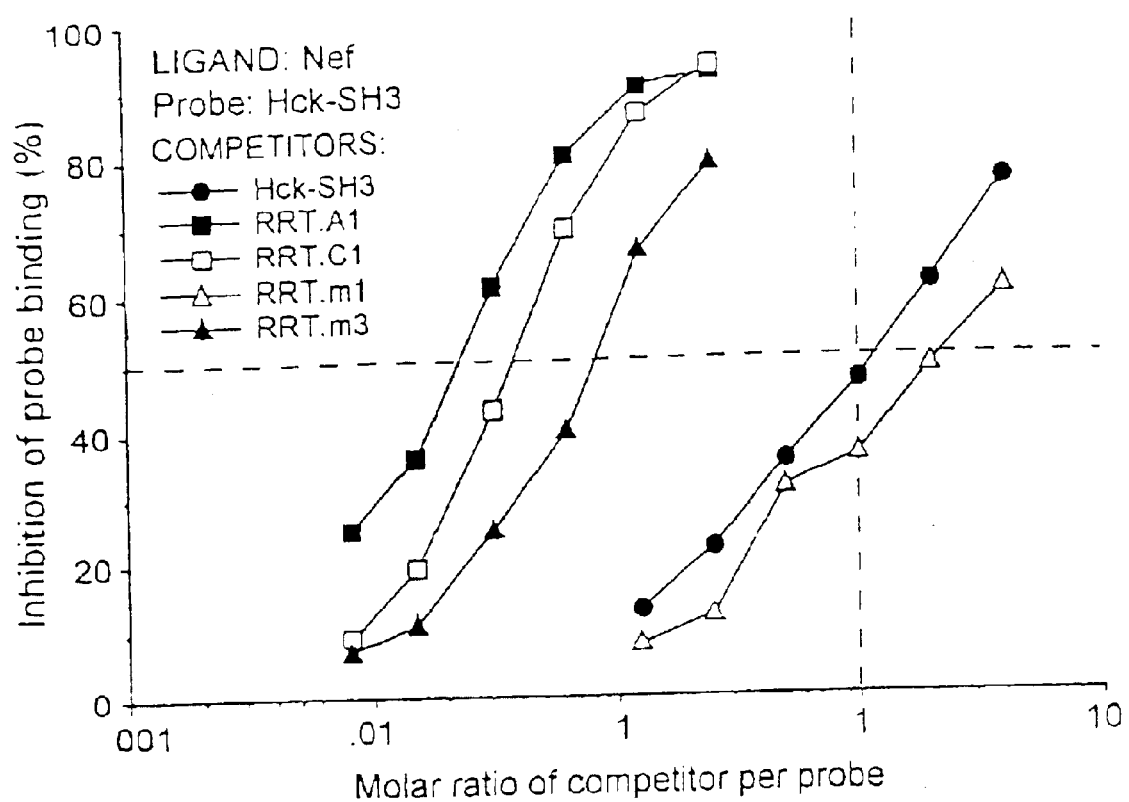
FIG. 2A.

As evident from FIG. 2A and Table I, all RRT-SH3 proteins from late rounds of selection bound to Nef substantially better than Hck-SH3. Many of these RRT-SH3's were able to compete more than 50% of binding of Hck-SH3 to Nef even when present in a 20-fold lower concentration, indicating a $K_D$ value below 12 nM. Although such avidly binding RRT-SH3 domains were found in all RT-loop sequence families, the Ser-Pro-Phe tripeptide motif was frequently present in clones that had showed the strongest binding to Nef. The proteins RRT.A1, RRT.B6, and RRT.C1 could consistently inhibit 50% or more of the Hck-SH3 binding even at concentration ratios lower than 1:35, corresponding to $K_D$ values as low as 7 nM.

Figure 2B:
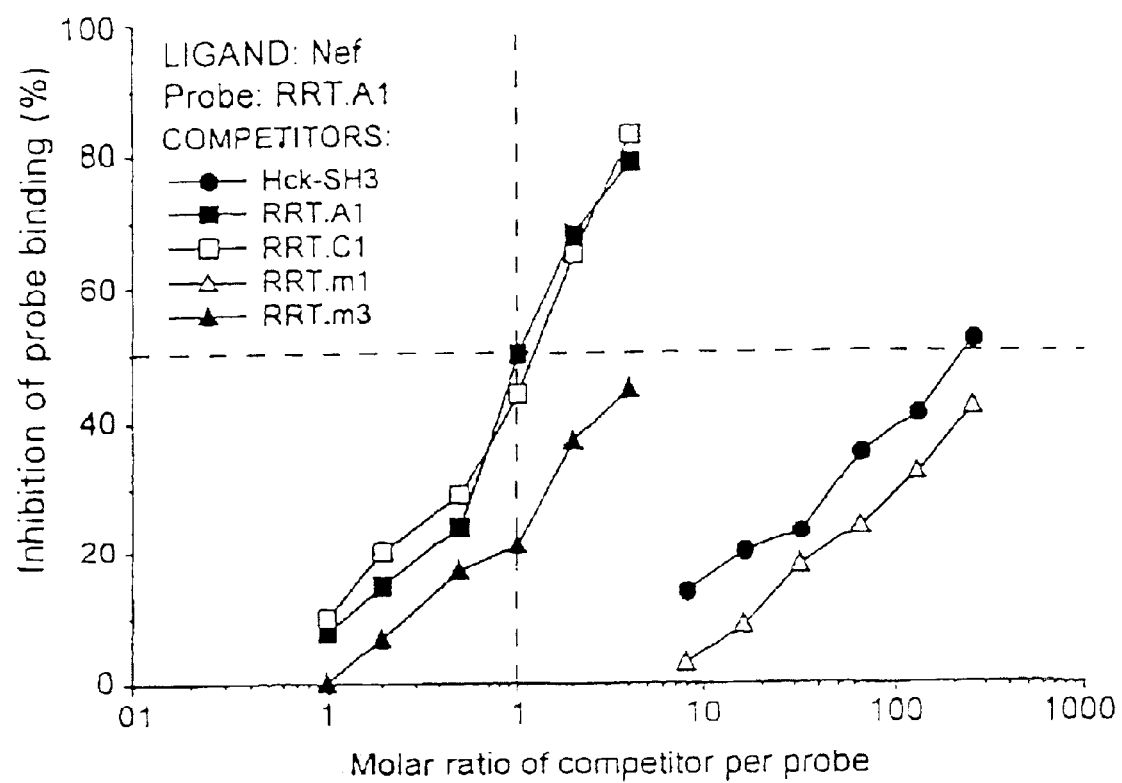
FIG. 2B. Data from two representative experiments measuring binding of four different RRT-SH3 domains to immobilized Nef based on their ability to compete with labeled Hck-SH3 (FIG. 2A) or RTT-A1 (FIG. 2B). The assay conditions were essentially the same in both cases (see Methods in Example 1), exept that ten times more Hck-SH3 (66 nM, 2A) than RTT.A1 (7 nM. 2B) was used as a probe. The degree of inhibition of probe binding to Nef caused by the added competitors is shown on the y-axis, and the 50% level is indicated by the horizontal dashed line. The concentration of the competitor relative to the probe (ranging 1:128 to 4:1 for Hck-SH3, and 1:9 to 256:1 for RRT.A1) is shown on the x-axis, and the point where the probe and the competitor were present in equimolar amounts is indicated by the vertical dashed line. As expected, in both cases when the same SH3 domain was used as a probe and a competitor, the inhibition curves passed very close to the point where the dashed lines crossed. All RRT-SH3 domains were tested at least three times, and the summary of these data is shown in Table I.

These remarkably high affinities were also supported by experiments in which 96-well plate assay was formatted in the reverse configuration, using a high-affinity RRT-SH3 domains (RRT.A1) as the probe and Hck-SH3 or one of the other RRT-SH3 proteins as the competitor (FIG. 2B). The ability of the different RRT-SH3 proteins to compete with RRT.A1 correlated well with their relative capacities in inhibiting Hck-SH3 binding. Notably, Hck-SH3 was a very poor competitor of the RRT.A1/Nef interaction, and was able to cause a 50% inhibition only when added in more than a 100-fold excess of RRT.A1 used as a probe (7 nM vs. >0.85 $\mu$M). As when using Hck-SH3 as the probe, the homotypic competition of with an equimolar amount of unlabeled RRT.A1 resulted in an expected 50% inhibition of binding. Thus, this reverse configuration assay confirmed our conclusions regarding the superior binding affinities of the selected RRT-SH3 proteins, and suggested that their affinities could be even higher than estimated using Hck-SH3 as the probe.

RRT-SH3 Domains Recognize Nef by Divergent Strategies

A discussed above, an isoleucine residue in the RT-loop of Hck-SH3 has been shown to be important for its binding to Ncf. The aliphatic side chain of this Ile residue fits into a hydrophobic pocket formed in part by the Nef residue $Phe^{90}$. Mutation of this phenylalanine into an arginine (creating a mutant referred to as NefR90 in the following) greatly diminishes the affinity of Hck-SH3 binding ($K_D$ 1.99 $\mu$M). While this interaction provides a structural explanation for the affinity of Hck-SH3, other modes of molecular recognition of the Nef SH3-ligand surface could also be envisioned. Therefore, we were interested in examining whether the Nef-selected RRT-SH3 domains also depended on a similar hydrophobic interaction, and would therefore also be affected by the F90R mutation in Nef.

Figure 3:
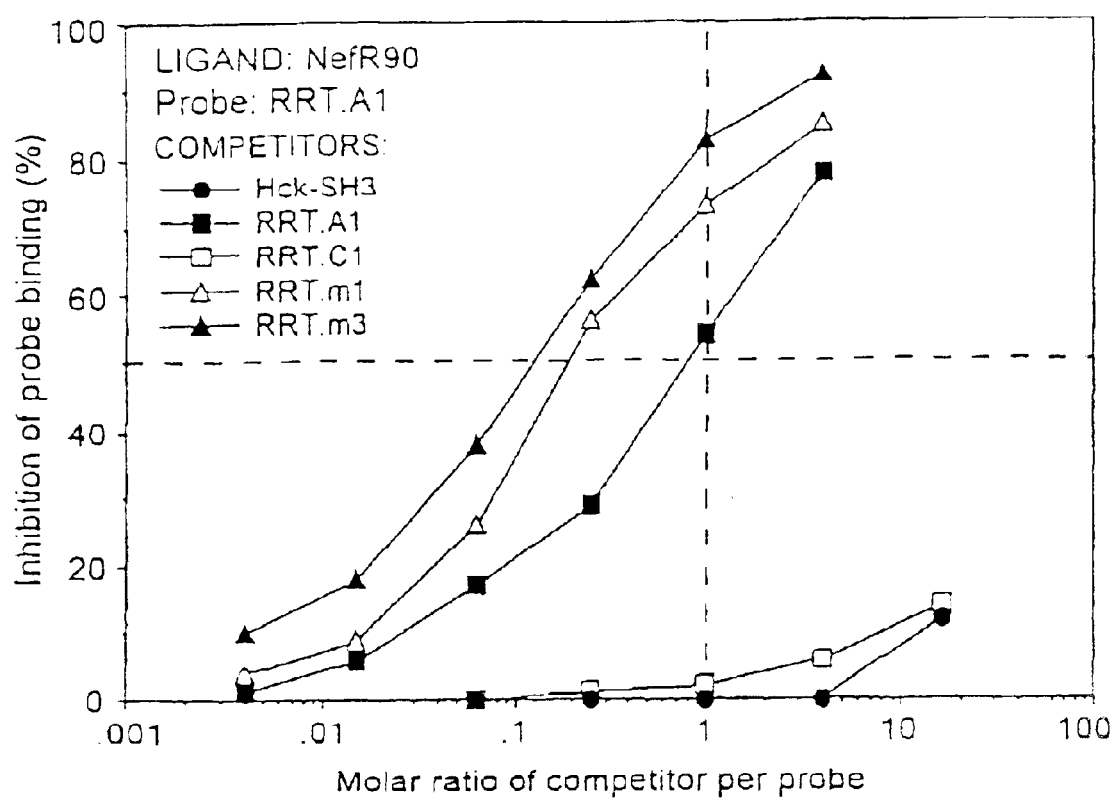
FIG. 3. Binding of selected RRT-SH3 domains to a Nef variant carrying a F90R mutation. NefR90 was used a ligand for biotinylated RRT.A1 (66 nM) in the presence of unlabeled SH3 domains at relative concentrations ranging from 1:256–16:1. Summary of similar data on all tested RRT-SH3 domains is presented in Table I.

Due to the low affinity of the Hck-SH3/NefR90 interaction it was not possible to develop a quantitative 96-well plate assay based on binding of Hck-SH3 to immobilized NefR90. In contrast, strong binding and an adequate signal-to-noise ratio were observed when biotinylated RRT.A1 protein was tested as a probe. This indicated that the RRT-SH3 domain RRT.A1 did not critically depend on the $Phe^{90}$ residue in its binding to Nef, and allowed us to examine the relative affinities of the rest of the RRT-SH13 proteins for NefR90 based on their ability to compete with RRT.A1 (FIG. 3).

As expected, Hck-SH3 was a very inefficient competitor of the RRT.A1/NefR90 interaction (FIG. 3 and Table I), and failed to cause a 50% inhibition of binding even when used in a 16-fold molar excess (66 nM vs. 1.1 $\mu$M), which was the highest practical competitor:probe ratio in the NefR90-assay. Based on the $K_D$ value 1.99 $\mu$M previously measured for the Hck-SH3/NefR90 complex (Manninen et al. 1998. Virology. 250, 273–82), the absolute affinity of RRT.A1 for NefR90 was therefore estimated to be 100 nM or better. When the other Nef-selected RRT-SH3 proteins were tested as competitors for RRT.A1 binding, widely varying affinities for NefR90 were observed (FIG. 3 and Table 1). Some RRT-SH3's (such as RRT.A2 and RRT.B4) competed efficiently with RRT.A1 binding, indicating that like RRT.A1 they also were relatively insensitive to the F90R change. In contrast, other RRT-SH3 s (such as RRT.B1 and RRT.C1) were almost completely unable to interfere with RRT.A1/NefR90 complex formation even when tested at high concentrations. Thus, some of the high-affinity RRT-SH3 proteins shared with Hck-SH3 a mode of binding to Nef in which the Nef $Phe^{90}$ plays a dominant role, whereas others appeared to recognize Nef by dissimilar mechanisms, and bound well also to NefR90.

RRT-SH3 Specific for the NefR90 Mutant

The above finding suggested that, depending on their RT-loops, the selected SH3 domains could recognize ligands by divergent molecular strategies. Encouraged by this observation we wanted to extend this concept further by engineering SH3 domains with entirely redirected binding specificities. To this end, we decided to develop RRT-SH3 domains that would not bind to wild-type Nef, but instead would show strong affinity for the NetR90 mutant. Thus, binding of such RRT-SH3 domains would be strictly dependent on interactions mediated by structural determinants involving the mutant $Arg^{90}$ residue, and would bear little resemblance to the natural recognition of Nef by Hck-SH3. For this purpose Nef-F90R was used as an affinity selection reagent, as described above for wild-type Nef, except that in some experiments an excess of soluble wild-type Nef was also included to enhance selection RRT-SH3 proteins that would primarily recognize $Arg^{90}$-dependent determinants.

The most frequently observed RT-loop sequences of the NefR90-selected RRT-SH3 domains are shown in the bottom panel of Table T. Although these selection experiments were carried out almost as extensively (6 independent experiments) as in the case of wild-type Nef, equally obvious consensus RT-loop sequences were not apparent. As seen in Table I, however, certain amino acids were favored in some positions, such as the dipeptide Phe-Leu in the positions 3/6 and 4/6, Glu in 1/6, Ala in 2/6, and Ser in 4/6. Notably, these NefR90-selected RT-loops did not contain any of the sequence motifs that characterized the Nef-selected RRT-SH3 domains. Also, with one exception (RRT.m4), the Ser 2/6 that was invariant in the Ncf-selected clones was absent from the NefR90-selected RRT-SH3 domains.

As shown in FIG. 3 and Table I, all RRT-SH3 proteins selected for NefR90 binding (RRT.m1 through RRT.m4) could efficiently compete with binding of the clone RRT.A1 to NefR90, and were estimated to have affinities 8- to 4-fold higher than the "dual-specific" clone RRT.A1. Remarkably, binding of some of these NefR90-selected RRT-SH3 domains was critically dependent on the mutant $Arg^{90}$ residue, whereas others appeared to be "dual-specific". An example of the latter was RRT.m3, which besides being a potent inhibitor of the RRT.A1/NefR90 interaction, also competed well with RRT.A1 in binding to Nef. In contrast, the clones RRT.m1 and RRT.m4 were virtually unable to compete with RRT.A1 for binding to Nef (FIG. 3 and Table I). Thus, only a small fraction of the strong affinity of RRT.m1 and RRT.m4 towards NefR90 was contributed by structural determinants that did not involve the mutant $Arg^{90}$ residue. Due to this residual ($Arg^{90}$-independent) affinity, however, they could still compete with the Hck-SH3/Nef interaction. Nevertheless, the fact that these clones bound to NefR90 at least 100-times better than Hck-SH3 or some of the Nef-selected clones (such as RRT.C1) clearly indicated that they had been provided with a strikingly novel binding specificity, which targeted them for a high-affinity interaction that depended on an artificially created epitope in their ligand.

What is claimed is:

1. A method for generating proteins containing artificial SH3 domains having ligand binding affinity that is higher than the affinity of corresponding wild-type SH3 domain which comprises:
   a) producing a collection of DNA fragments encoding SH3 domains containing randomized mutations in a variable domain of an RT-loop (RRT-SH3 domains) that corresponds to amino acids 69–74 of Hck,
   b) generating recombinant libraries comprising said variable RT-loon domains,
   c) subjecting said libraries to affinity or functional selection steps to identify non-naturally occurring RT-loop domains, and
   d) selecting proteins containing domains with a binding affinity that is higher than the binding affinity of the corresponding wild-type SH3 domain.

2. The method according to claim 1, wherein the amino acid residues in the variable region of the RT-loop that are replaced comprise six amino acid residues that immediately follow a conserved stretch of amino acids having an ALYDY (SEQ ID NO:1) consensus sequence.

3. The method according to claim 1, wherein the recombinant libraries comprise said RRT-SH3 domains in plasmid, phagemid or viral vectors.

4. The method according to claim 2, wherein the six amino acids that are replaced in the RT-loop are replaced with a peptide motif derived from Hck-SH3 and which binds to HIV-1 Nef protein selected from the group consisting of XSWSXX (SEQ ID NO:28), XSPFXX (SEQ ID NO:30) and XSXFPW (SEQ ID NO:32), wherein X is any amino acid.

5. The method of claim 4, wherein X is an amino acid selected from the group consisting of V, F, D, M, P, S, T, W, and Y (SEQ ID NOS:29 and 30).

6. The method of claim 4, wherein the peptide motif is selected from the group consisting of VSWSPD (SEQ ID NO:6), FSWSDT (SEQ ID NO:7), DSWSTS (SEQ ID NO:8), YSWSDM (SEQ ID NO:9), WSPFPS (SEQ ID NO:10), DSPFSF (SEQ ID NO:11), FSPFSF (SEQ ID NO:12), FSPFDW (SEQ ID NO:13), SSPFDW (SEQ ID NO:14), YSPFSW (SEQ ID NO:15), TSPFPW (SEQ ID NO:16), YSFFPW (SEQ ID NO:17), YSDFPW (SEQ ID NO:18) and DSWFPW (SEQ ID NO:19).

* * * * *